United States Patent [19]

Luther

[11] Patent Number: 4,964,854
[45] Date of Patent: Oct. 23, 1990

[54] INTRAVASCULAR CATHETER ASSEMBLY INCORPORATING NEEDLE TIP SHIELDING CAP

[75] Inventor: Ronald B. Luther, Newport Beach, Calif.

[73] Assignee: Luther Medical Products, Inc., Tustin, Calif.

[21] Appl. No.: 299,302

[22] Filed: Jan. 23, 1989

[51] Int. Cl.⁵ ............................................. A61M 5/178
[52] U.S. Cl. .................................. 604/166; 604/168; 604/263
[58] Field of Search ................... 604/52, 53, 110, 163, 604/171, 192, 198, 239, 263, 164, 165, 166

[56] References Cited

U.S. PATENT DOCUMENTS

| | | | |
|---|---|---|---|
| 1,596,754 | 4/1926 | Monchelle | 604/282 |
| 3,030,953 | 4/1962 | Koehn | 604/166 |
| 3,225,762 | 12/1965 | Guttman | 128/214 |
| 3,352,306 | 11/1967 | Hirsch | 128/214.4 |
| 3,459,183 | 8/1969 | Ring et al. | 128/214.4 |
| 3,463,152 | 8/1969 | Sorenson | 128/214.4 |
| 3,536,073 | 10/1970 | Farb | 128/214.4 |
| 3,598,118 | 8/1971 | Warren | 128/214.4 |
| 3,612,050 | 10/1971 | Sheridan | 128/214.4 |
| 3,625,741 | 12/1971 | Stoy et al. | 117/75 |
| 3,788,318 | 1/1974 | Kim et al. | 128/214.4 |
| 3,809,081 | 5/1974 | Loveless | 128/214.4 |
| 3,811,449 | 5/1974 | Gravlee et al. | 128/343 |
| 3,833,003 | 9/1974 | Taricco | 128/347 |
| 3,946,741 | 3/1976 | Adair | 128/347 |
| 4,020,835 | 5/1977 | Nordstrom et al. | 128/214.4 |
| 4,160,450 | 7/1979 | Doherty | 128/214.4 |
| 4,177,814 | 12/1979 | Knepshield et al. | 128/348 |
| 4,183,884 | 1/1980 | Wichterle et al. | 264/41 |
| 4,434,797 | 3/1984 | Silander | 128/343 |
| 4,468,224 | 8/1984 | Enzmann et al. | 604/247 |
| 4,480,642 | 11/1984 | Stoy et al. | 128/341 |
| 4,500,312 | 2/1985 | McFarlane | 604/263 |
| 4,515,583 | 5/1985 | Sorich | 604/239 |
| 4,588,398 | 5/1986 | Daugherty et al. | 604/265 |
| 4,613,329 | 9/1986 | Bodicky | 604/163 |
| 4,631,057 | 12/1986 | Mitchell | 604/198 |
| 4,652,256 | 3/1987 | Vaillancourt | 604/52 |
| 4,664,653 | 5/1987 | Sagstetter et al. | 604/197 |
| 4,664,654 | 5/1987 | Strauss | 604/198 |
| 4,676,783 | 6/1987 | Jagger et al. | 604/171 |
| 4,702,738 | 10/1987 | Spencer | 604/198 |
| 4,747,831 | 5/1988 | Kulli | 604/110 |
| 4,790,817 | 12/1988 | Luther | 604/53 |
| 4,790,828 | 12/1988 | Dombrowski | 604/198 |
| 4,846,805 | 7/1989 | Sitar | 604/165 |
| 4,846,809 | 7/1989 | Sims | 604/198 |
| 4,846,811 | 7/1989 | Vanderhoof | 604/263 |
| 4,880,410 | 11/1989 | Rossmark | 604/110 |

FOREIGN PATENT DOCUMENTS

| | | |
|---|---|---|
| 0139872A | 5/1985 | European Pat. Off. . |
| 2636812 | 2/1978 | Fed. Rep. of Germany ...... 604/160 |
| 1092011 | 1/1954 | France . |
| 84/04462 | 11/1984 | PCT Int'l Appl. ............... 128/341 |

OTHER PUBLICATIONS

"Introducing the ICU HR ™ Needle (High Risk)", by ICU Medical, Inc., 4 pages.

Primary Examiner—John D. Yasko
Assistant Examiner—Adam J. Cermak
Attorney, Agent, or Firm—Stetina and Brunda

[57] ABSTRACT

Disclosed is an "over-the-needle" type catheter assembly which incorporates a shield operative to prevent inadvertant needle trauma after the needle has been withdrawn from the surrounding catheter sheath. The device of the invention comprises a tubular catheter sheath having an elongate piercing member (e.g. a needle) initially disposed in an "assembled" position within the lumen of the tubular sheath. The elongate piercing member is subsequently withdrawable to a "retracted" position outside the lumen of the tubular sheath. A shield is incorporated into the catheter assembly and is operative to attach to and shield the tip of the elongate piercing member when it is withdrawn from its initial "assembled" position within the tubular sheath. Such shield thereby serves to prevent the elongate piercing member from causing inadvertant puncture wounds and the like.

10 Claims, 3 Drawing Sheets

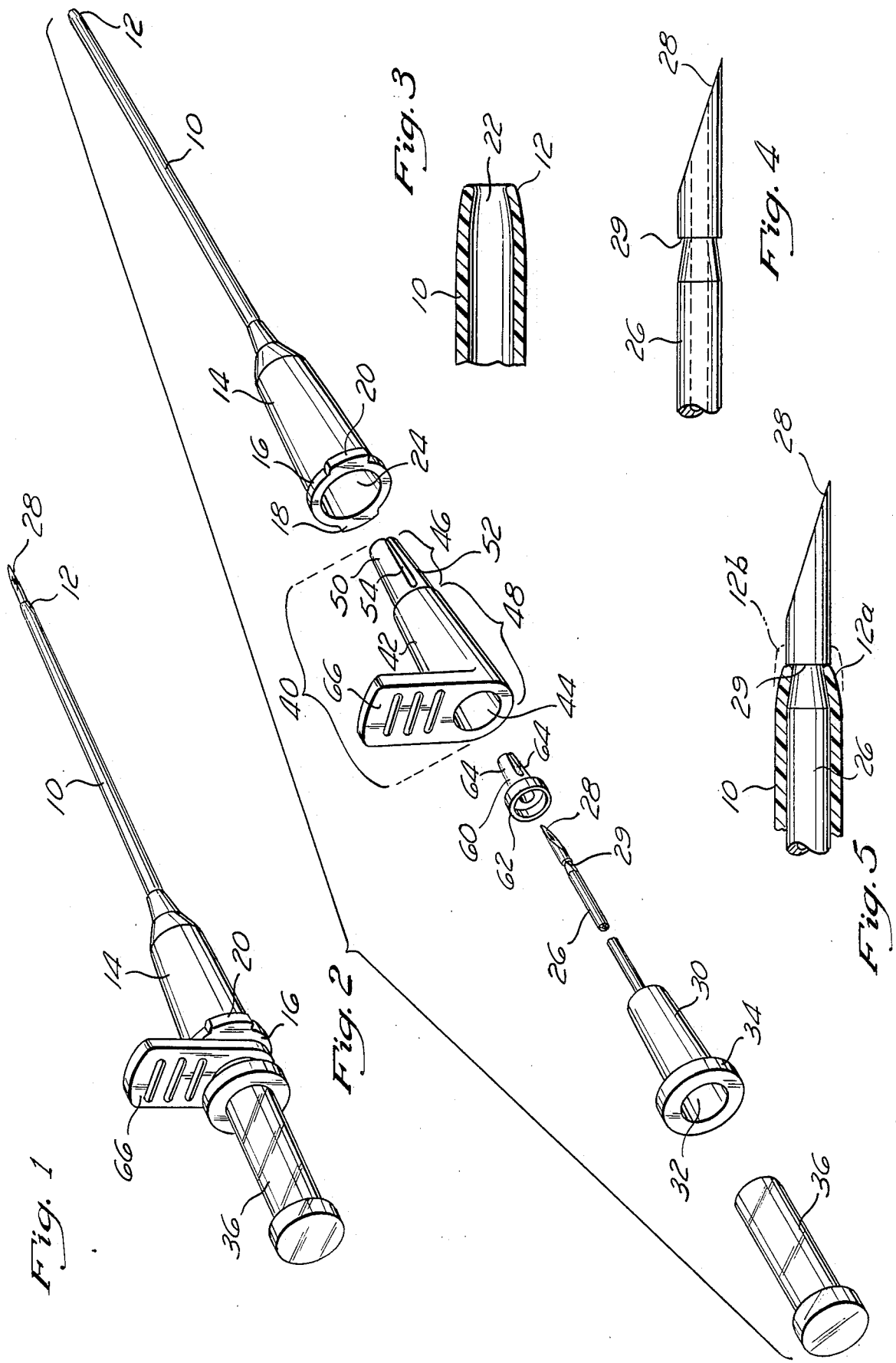

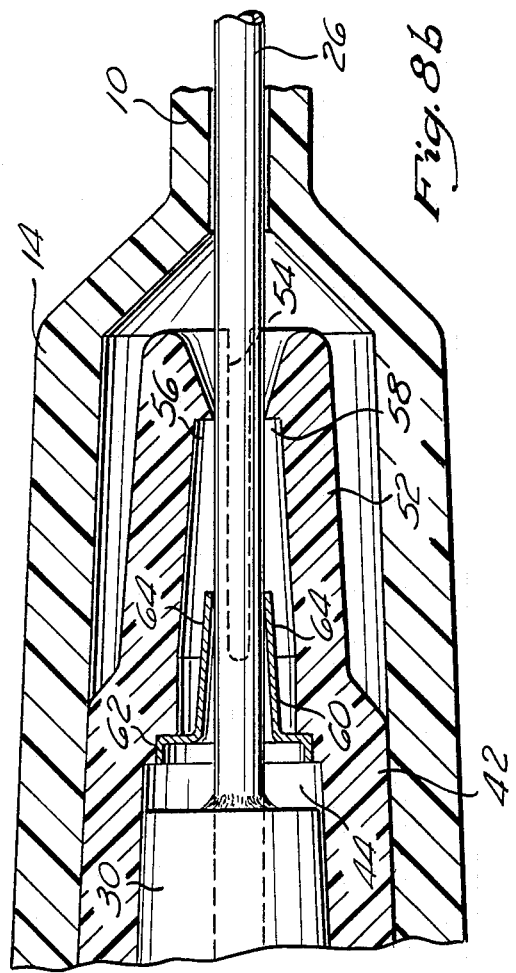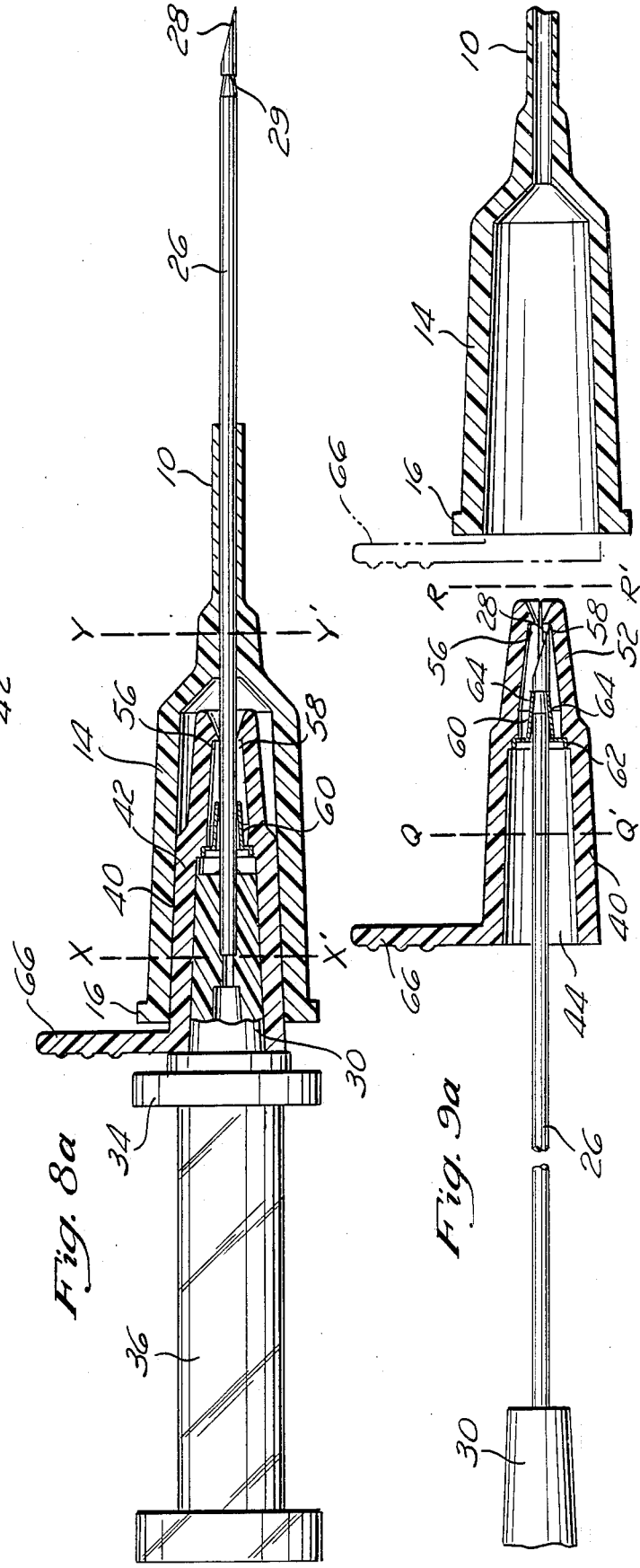

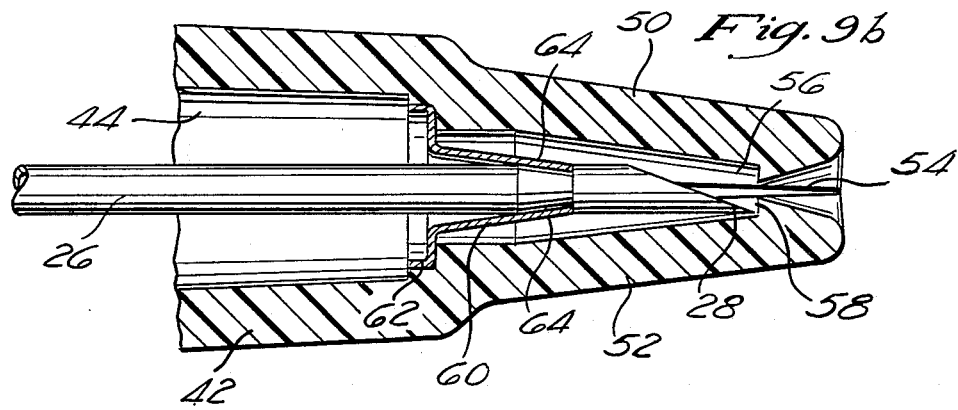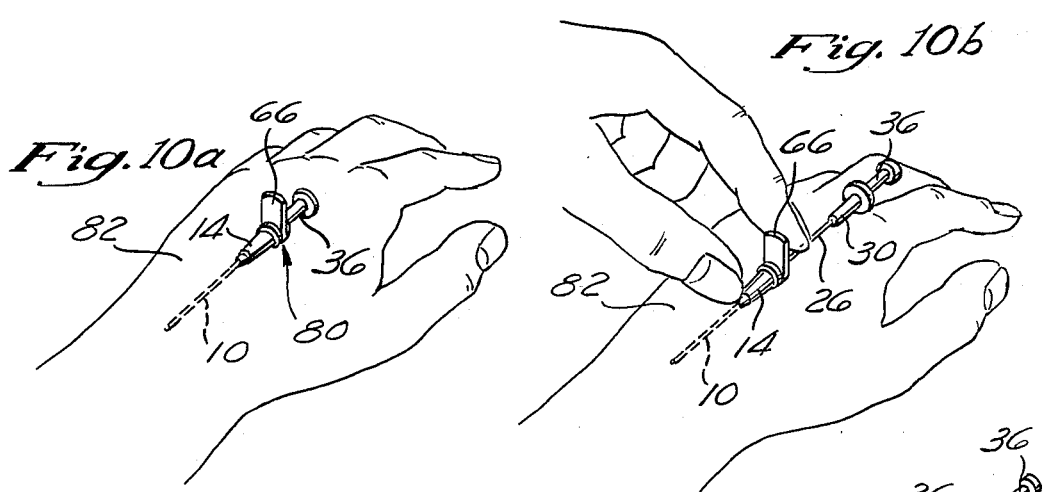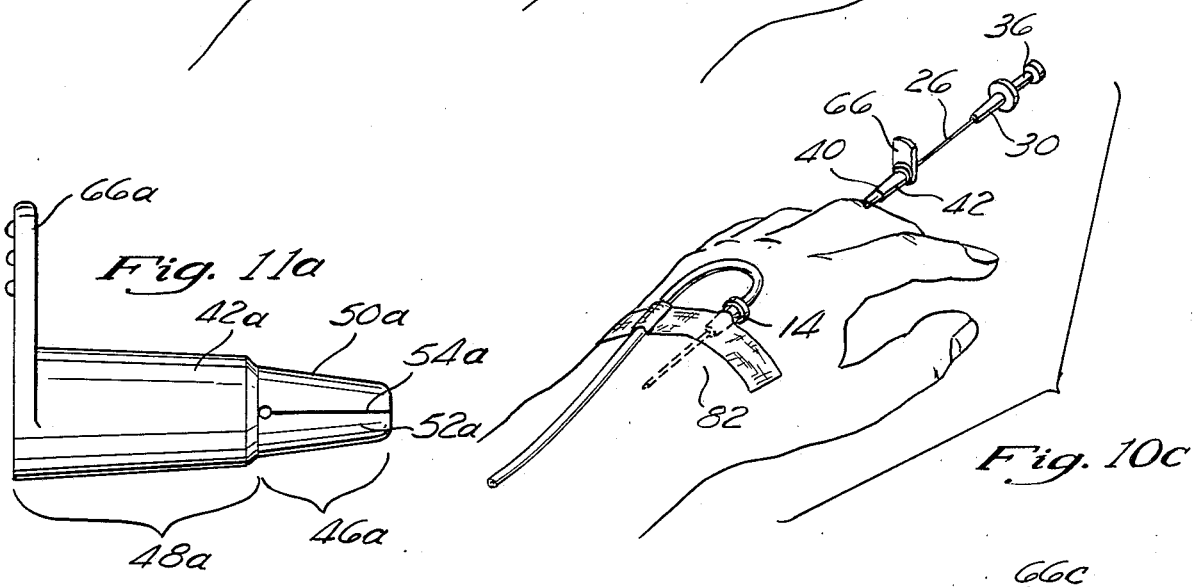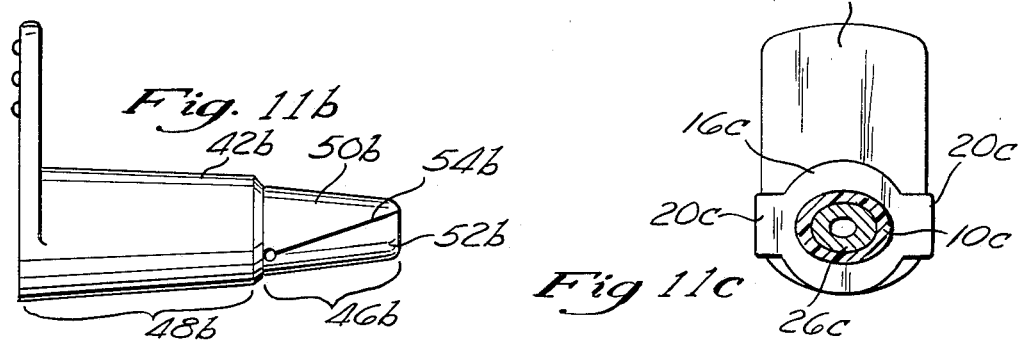

INTRAVASCULAR CATHETER ASSEMBLY INCORPORATING NEEDLE TIP SHIELDING CAP

FIELD OF THE INVENTION

The present invention pertains generally to the medical arts and more particularly to an improved "over-the-needle" type intravascular catheter which incorporates a shielding means operative to prevent inadvertant needle trauma after the needle has been withdrawn from the surrounding catheter sheath.

BACKGROUND OF THE INVENTION

It is common practice in the medical arts to insert various types of flexible catheters or cannulae into blood vessels for purposes of gaining and maintaining vascular access and/or for monitoring of intravascular pressures. One type of intravascular catheter assembly which is particularly suited for percutaneous insertion comprises what is known in the art as the "over-the-needle" (hereinafter "OTN") type. A typical OTN catheter assembly comprises a pliable catheter sheath having a distal end, a proximal end, and a hollow lumen extending axially therebetween A generally rigid introducer needle or other elongate piercing member is disposed axially within the lumen of the catheter such that the beveled distal tip of the needle extends slightly beyond the distal tip of the exteriorly disposed catheter. The protruding distal tip of the needle facilitates puncture of the skin and underlying tissues. After the assembly has been advanced to a desired point (e.g. such that the distal portion of the catheter sheath resides within a blood vessel) the needle is proximally withdrawn and removed from the catheter sheath. The catheter sheath is then allowed to remain within the blood vessel for purposes of continued vascular access and/or transmission of pressure pulses.

One drawback associated with the use of standard OTN-type catheters is that the sharpened distal tip of the introducer needle becomes exposed and unguarded when the needle is withdrawn from the surrounding catheter sheath. Such exposure of the needle tip is known to result in occasional injury (e.g. inadvertant skin puncture or other trauma) to health care workers and others who routinely handle such needles. The occurrence of such inadvertant needle trauma is cause for extreme concern due to the transmissibility and potential seriousness of various blood-borne infections, including hepatitis, Acquired Immune Deficiency Syndrome (AIDS) and others. Thus, the development of new, safer needles and catheter assemblies remains a desirable goal.

In efforts to minimize the occurrence of inadvertant needle induced trauma, a number of modified OTN-type catheter assemblies have incorporated means for shielding or covering the distal tip of the needle after it has been withdrawn from the surrounding catheter. Such modified OTN catheter assemblies are, however, less than optimal in that they are cumbersome, bulky, expensive, and/or require substantial manual manipulation in order to effect the desired covering or shielding of the needle. It is therefore desirable to provide a simple needle tip covering and shielding device which is capable of being attached to the needle in an essentially automatic manner, thereby requiring little or no manual endeavor on the part of the operator.

BRIEF SUMMARY OF THE INVENTION

The present invention overcomes the aforestated shortcomings of the prior art, and others, by providing an OTN catheter assembly which incorporates a needle tip shielding means which is virtually automatic in operation and which attaches to the needle tip in such a manner as to permit routine withdrawal and disposal of the needle following insertion of the catheter sheath.

The present invention finds particular utility in connection with OTN catheter assemblies of the type routinely inserted into peripheral blood vessels for purposes of intravenous drug/fluid infusion and/or monitoring of pressures. It must be appreciated, however, that the invention has much broader applicability and may be used in connection with virtually any medical device wherein a needle or other sharp-tipped object is positioned within, and subsequently withdrawn from, the lumen of a surrounding tubular structure Examples of other types of devices which may utilize the present invention include but are not limited to: various trocars for intra-abdominal and/or intra-thoracic insertion, over-the- needle cannulae of the type used in performing suprapubic cystotomies and tubular "introducers" of the type commonly used to facilitate passage and positioning of long guide wires and cardiovascular catheters.

In accordance with the invention, there is provided an OTN catheter assembly comprising a catheter sheath having a distal end, a proximal end, and an inner lumen extending. A generally rigid elongated piercing means (e.g.: an introducer needle, solid stylet, or needle/stylet combination) is disposed axially within the lumen of the catheter sheath such that the sharpened distal tip of the piercing means extends beyond the distal tip of the catheter sheath. Such distal protrusion of the piercing means facilites percutaneous insertion of the catheter assembly into an underlying structure, such as a blood vessel. After the distal portion of the assembly has been percutaneously inserted in the above-described fashion, the piercing means is then withdrawn proximally from the surrounding catheter sheath with the sheath being permitted to remain in the blood vessel or other anatomical structure. A shielding means is incorporated into the assembly and is operative to attach to and shield the sharpened tip of the elongate piercing means following withdrawal thereof. The attachment of such shielding means to the needle/piercing means tip is intended to prevent the occurrence of inadvertant puncture injuries or other skin-penetration trauma as may occur in health care workers and others who handle such needle/piercing means following withdrawal thereof.

In accordance with a further aspect of the invention, there is provided a catheter assembly of the foregoing character wherein the shielding means comprises a generally frusto-conical body having an inner bore extending therethrough. A pair of internally notched lobes are formed on the distal end of the body. A catch means, such as a spring ferrule, is positioned within the inner bore. Additionally, one or more notches, depressions, shoulders, grooves, or other engagement means are formed on the outer surface of the elongate piercing means, so as to interact with the spring ferrule as the piercing means is withdrawn therefrom. Thus, as the piercing means is withdrawn proximally through the catheter sheath, the spring ferrule of the shielding means will engage the notch(s), depression(s), groove(s), shoulder(s), or other engagement means of the piercing means. As a result of such interaction between the spring ferrule and the engagement means, any further proximally directed movement of the needle will serve to pull the needle tip shielding component with it in the proximal direction Additionally, the notches formed on the inner surfaces of the distal lobes will be configured such that, when the engagement means of the piercing member comes in contact with or interacts with the spring ferrule, the sharpened distal tip of the piercing means will drop into or be captured by at least one of the notches. As a result, the needle tip shielding component will become firmly attached to the piercing means tip and the sharpened piercing means tip will be covered or shielded so as not to cause injury.

In accordance with a further aspect of the invention one or more finger tabs may extend outwardly from the body of the needle tip shielding component. Such finger tab(s) may be sized, configured, and positioned such that, when the user of the device exerts finger pressure thereagainst, the needle tip sheiding component will be held in its initial "assembled" position (e.g. nested within the inner bore of the cannula hub). Such finger pressure may be maintained during withdrawal of the needle/piercing means until the shielding component engages or otherwise attaches to the needle. Thereafter, the finger pressure may be removed. Further proximally directed extraction of the needle/piercing means will then serve to pull the shielding component away from its initial assembled position Thus, in short, the finger tab will permit the user to hold the shielding component in position until it is firmly attached to the needle/piercing means tip.

A principal object of the invention is to prevent the transmission of blood-borne diseases by minimizing the occurrence of inadvertant needle puncture and/or trauma.

A further object of the invention is to provide an improved intravascular catheter assembly which is practical, relatively easy to use, and which may be reproduceably manufactured.

Further objects and advantages will become apparent to those skilled in the art upon reading and understanding of the following detailed description and the accompanying drawings.

BRIEF DESCRIPTION OF THE DRAWINGS

FIG. 1 is a perspective view of a preferred over-the-needle catheter assembly of the present invention;

FIG. 2 is an exploded perspective view showing the individual components of a preferred over-the-needle catheter assembly of the present invention;

FIG. 3 is a longitudinal sectional view of the distal tip of a catheter sheath of the present invention;

FIG. 4 is a side elevational view of the distal portion of a preferred introducer needle of the present invention;

FIG. 5 is a longitudinal sectional view showing the distal portion of a preferred introducer needle of the present invention operatively disposed within the lumen of a flexible catheter sheath;

FIG. 6 is an elevational view of a spring ferrule which forms an element of the needle tip shielding component of one preferred embodiment of the invention;

FIG. 7 is a longitudinal sectional view of the distal portion of a preferred needle tip shielding component of the present invention; and FIG. 8a is a longitudinal sectional view of a preferred over-the-needle catheter assembly of the present invention with the distal portion of the catheter sheath cut away so as to expose the shaft of the introducer needle;

FIG. 8b is an enlarged longitudinal sectional view of the portion of the device extending between lines X—X' and Y—Y' of FIG. 8a;

FIG. 9a is an exploded longitudinal sectional view of a preferred over-the-needle catheter assembly of the present invention following withdrawal of the introducer needle to its "retracted" position with resultant attachment thereto of the needle tip shielding component;

FIG. 9b is an enlarged longitudinal sectional view showing the portion of the device lying between lines Q—Q' and R—R' of FIG. 9a;

FIGS. 10a through 10c depict separate steps in the method by which the preferred over-the-needle catheter assembly of the present invention is used;

FIGS. 11a and 11b are elevational views of modified needle tip shielding components of the present invention; and FIGS. 11c is a frontal (proximally directed) cross-sectional view of a modified catheter assembly of the present invention incorporating an ovoid needle and catheter sheath.

DETAILED DESCRIPTION OF THE PREFERRED EMBODIMENTS

The accompanying drawings are provided for purposes of illustrating presently preferred embodiments of the invention and are not intended to limit the scope of the invention in any way.

A preferred OTN catheter assembly of the present invention comprises a flexible catheter sheath 10 having a tapered distal tip 12 and a proximal hub 14. As shown, the hub 14 comprises a standard female Leur-type connector having a radial flange 16 with lateral engagement ears 18, 20 extending from either side thereof. A hollow inner lumen 22 extends longitudinally through the catheter sheath 10. The lumen 22 opens distally through the distal tip 12 of the sheath 10 and proximally into the hollow inner bore 24 of the catheter hub 14. A rigid introducer needle 26 is initially disposed longitudinally within the inner lumen 22 of the catheter sheath 10 such that the beveled distal tip 28 of the needle emerges from and extends beyond the distal end 12 of the catheter sheath 10. Thus, when fully assembled, the protruding distal tip 28 of the needle 26 facilitates puncture of the skin and underlying tissues as necessary to permit insertion of the catheter sheath 10 into a desired blood vessel.

The needle 26 is provided with an inner lumen extending longitudinally between the distal tip 28 of the needle and the proximal hub 30 thereof. The lumen of the needle opens proximally into the hollow inner bore 32 of the needle hub 30. An annular flange 34 is formed about the proximal end of needle hub 30 so as to permit attachment of syringes and the like when desired. Although a single piece annular flange 34 is shown, it should be appreciated that any acceptable arrangement, including a more standard "Luer-lock" flange may be formed on the needle hub 30 as desired.

A transparent cap member 36 is slidably attachable to the proximal end of the needle hub 30 and is frictionally held in place so as to be easily pulled away and discarded when its use is no longer desired The cap member 36 may be perforated or otherwise vented to permit air from the interior thereof to be exhausted as blood or fluid flows thereinto.

The inventive needle tip shielding component 40 of this presently preferred embodiment is initially incorporated into the catheter assembly Such needle tip shielding component 40 attaches to and shields the sharpened distal tip 28 of needle 26 as the needle 26 is proximally withdrawn from its initial position within flexible catheter sheath 10.

The preferred needle tip shielding component 40 comprises a generally frusto-conical body 42 having an inner bore 44 extending therethrough. The body 42 of the needle tip shielding component is generally divisible into a distal portion 46 and a proximal portion 48. The distal portion 46 of the body 42 comprises an upper lobe 50 and a lower lobe 52. A slit 54 separates the upper lobe 50 from the lower lobe 52 and extends transversely through the entire width of the distal portion 46. The inner surfaces of the lobes 50 and 52 are undercut at their distal ends so as to form angular notches 56,58 therewithin.

A spring ferrule 60 is inserted, mounted, or formed within the inner bore 44 of the body 42. The spring ferrule 60 comprises an annular ring 62 having a plurality of spring leaflets 64 extending therefrom. When positioned within the inner bore 44 of the needle tip shielding component body 42, the annular ring 60 will seat at or near the convergence of the proximal portion 48 and distal portion 46 thereof In such position, the spring leaflets 64 extend distally from the annular ring 60 and are slightly angled toward one another so as to be directly abutting or very close-spaced at their extreme distal ends. As such, the individual spring leaflets 64 of the ferrule 60 will ride upon and/or exert pressure against the outer surface of the needle shaft as needle 26 is passed or positioned therebetween.

Similarly, the slit 54 extending longitudinally between the upper 50 and lower 52 lobes of the body 42 will permit such lobes 50,52 to be spread apart in the direction of arrows B when the shaft of needle 26 is positioned therebetween As a result, the inner edges of the distal ends of lobes 50 and 52 will maintain contact with and press against the outer surface of the shaft of needle 26 when it is positioned therebetween. However, when the needle 26 is retracted or removed, the lobes 50, 52 will relax or snap together once again.

An engagement means comprising an annular shoulder 29 is formed about the outer surface of needle 26 near its distal tip 28. When fully assembled, the distal tip 12 of the flexible catheter sheath 10 may abut against or extend distally beyond the annular shoulder 29.

An embodiment wherein the distal tip 12 of the sheath 10 abuts directly against the annular shoulder 29 is represented by item 12a of FIG. 5. When the distal tip 12 of the catheter sheath 10 resides within the annular groove 29, as shown in item 12a of FIG. 5, it may be desirable or even necessary that the catheter sheath 10 be made of an expandable, stretchable, or swellable material so that the distal tip of the catheter may undergo sufficient dilation as to be passable over the shoulder. One such expandable or swellable catheter embodiment is made of material which, when placed in contact with blood or body fluid, will swell to a point where the inner diameter of the cannula lumen will be slightly greater than the outer diameter of the shoulder 29, thereby permitting proximally directed withdrawal of the needle 26 from the lumen of catheter 10.

Alternatively, the distal tip 12 of the catheter sheath 10 may, when fully assembled, be positioned distal to the annular shoulder 29 as shown by item 12b (dotted lines) of FIG. 5. In such alternative embodiment, the flexible catheter sheath 10 may be made of any suitable material and need not be capable of swelling or expanding as the tip 12b of the catheter sheath 10 does not abut the shoulder 29. Thus, the needle 26 may be proximally withdrawn therefrom without the need for swelling or expansion.

A generally rectangular tab 66 extends upwardly from the body 42 of the needle tip shielding apparatus 40. A surface of such tab 66 is textured to facilitate the application of finger pressure thereagainst, without the problem of slippage of the finger from the tab 66 surface.

It is recognized that the width and shape of the longitudinal groove 54 separating upper 50 and lower 52 lobes is a potentially important aspect of the invention in that the sharpened tip 28 of needle 26 could possibly avoid interaction with the angular notches 56, 58 of lobes 50, 52 if specifically oriented to permit the bevel of the needle 26 will slide along the groove 54 rather than being in alignment with the angular notches 56 or 58 of lobes 50 or 52. Such could result in non-capture of the needle tip 28 when the needle is retracted from its position within the catheter sheath 10. Thus, it is desirable that hashmarks or other indicia be formed on the needle hub and/or elsewhere on the assembly so as to insure that the needle remains in proper rotational orientation to effect the desired capture of the needle tip within angular notches 56, 58.

Alternative means for insuring proper capture of the needle tip 28 are shown in the alternative embodiments of FIGS. 11a, 11b, and 11c.

As shown in FIG. 11a, the longitudinal slit 54a separating lobes 50a and 52a may be extremely narrow such that, when in its relaxed position (i.e., without a needle passing therethrough), the lateral edges of upper lobe 54a and lower lobe 52a will directly abut one another. Such modified slit 54a does, however, extend fully through the distal portion 46a of the body 42a such that when the shaft of a needle is passed longitudinally therethrough, the lobes 54a and 52a will be able to spread apart slightly so as to accommodate such passage of the needle. Subsequently, when the needle is retracted the lobes 52a and 54a will snap back to their relaxed positions in abutment with one another.

In another alternative embodiment shown in FIG. 11b, the slot 54b is slightly angled as shown. Such angling of the slot 54b will prevent the needle tip from fully riding along the slot and escaping capture since the slot 54b is not parallel to the disposition of the needle as it passes through the body 52b. Such angling of the slot 54b, as shown, will not interfere with the function of the slot, i.e., the upper lobe 50b and lower lobe 52b will still spread apart slightly when the needle is passed therebetween and the lobe 50b, 52b will still spring together when the needle is removed.

Another approach to ensuring proper capture of the needle tip is through the use of an ovoid needle and ovoid catheter sheath, as shown in the alternative embodiment of FIG. 11c. For example, as shown in FIG. 11c, the shaft of the needle 26c and the surrounding catheter sheath 10c are of generally ovoid configuration so as to prevent rotational movement of the needle 26c within the sheath 10c. The result is that the rotational orientation of the needle 26c will remain constant during the percutaneous insertion procedure, thereby ensuring proper capture of the needle by the needle tip shielding means as the needle 26c is withdrawn. As shown in the cross-sectional view of FIG. 11c, the needle 26c and the catheter sheath 10c are of ovoid configuration. The needle hub 14c and its flange 16c remain generally round in configuration so as to accommodate standardized solution administration equipment, standard syringes, etc.

The various elements and components of the catheter assembly may be formed of any material(s) suitable for the intended purpose of the assembly In particular, it is preferable that the catheter sheath 10 be formed of material which is sufficiently physiologically inert to be capable of extended residence within a blood vessel or other body cavity without causing adverse effects therein. Such materials may include polytetrafluoroethylene and/or certain polyurethanes Additionally, in embodiments where expandability or swellability of the catheter sheath is requisite, appropriate materials will be selected to achieve such results.

OPERATION OF THE PREFERRED EMBODIMENTS

Having thusly described the various structural aspects of a presently preferred embodiment of the invention, the following description of its intended method of use will clarify and further explain the structure and function of its various elements.

FIGS. 10a through 10c illustrate three separate steps in the typical percutaneous insertion of an OTN intravascular catheter of the present invention. As shown in FIG. 10a, the intravascular catheter assembly 80 is initially inserted into a desired vein, such as one of the veins of the dorsal palmar surface 82 of the hand. After the assembly has been advanced to a point where a portion of the catheter sheath 10 resides within the desired blood vessel, the user will apply slight, distally directed finger pressure against the finger tab 66 while using the thumb to stabilize the cannula hub 14. Such finger pressure will serve to hold the needle tip shielding component 40 in its initial "assembled" position within the inner bore of the catheter hub 14 as the proximally directed withdrawal of the needle is begun.

During the application of such finger pressure, the user will grasp the hub 30 of needle 26 and withdraw needle 26 in a proximal direction as shown in FIG. 10b. Such proximally directed withdrawal of the needle 26 will continue until the movement of the needle stops, due to shoulder 29. When such point is reached, the distal tip of the needle will become nested in one of the angular notches (56,58 on FIG. 9b) of upper lobe 50 or lower lobe 52. Thereafter, the user may remove his finger from the tab 66 so as to permit the needle tip shielding component 40 to be withdrawn or pulled proximally from the inner bore 24 of the catheter hub 14. Accordingly, the needle 26, with the needle tip shielding component 40 firmly attached to the tip thereof, will become fully separated from the catheter 10 as shown in FIG. 10c. The needle 26 with the needle hub 30, cap 36, and needle tip shielding means 40 attached thereto may then be discarded in a routine manner. After retraction of the needle 26, a solution administration line 82 may be attached to the cannula hub 14 so as to permit infusion of solutions through the cannula sheath 10 into the desired vein. The solution administration line 82 and cannula hub 14 may then be taped in place as shown in FIG. 10C.

While the invention has been described herein with reference to presently preferred embodiments thereof, it must be appreciated that various additions, deletions, modifications, and alterations may be made to such embodiments without departing from the spirit and scope of the invention. For example, the internal and/or external design of the needle tip shielding component 40 may be altered such that the angular notches 56,58 differ substantially from the near-right-angle notches shown in FIGS. 7-9. To wit: the angular notches formed therein may comprise notches of any configuration suitable to effect the desired capture and shielding of the distal needle/piercing means tip Also, the annular groove or shoulder 29 of the needle shaft 26 may be replaced by any type of engagement means including detents, notches, ridges, apertures, grooves, depressions, or other configurations with corresponding changes being made in the design of the spring ferrule 60 so as to result in interaction and/or abutment of the spring ferrule 60 with the particular type of engagement means formed on the shaft of the needle or other elongate piercing member. Indeed, the leaves 64 need only be expansive enough to engage the particular detent or engagement notch necessary to prevent further proximal retraction of the needle 26. Thus, many engagement means and/or ferrule designs may be utilized to achieve such end. Accordingly, it is intended that all such additions, deletions, modifications, and alterations be included within the scope of the following claims and the equivalents thereof.

What is claimed is:

1. A catheter assembly comprising:
   a tubular sheath having a proximal end, a distal end, and an inner lumen extending axially therethrough;
   an elongate piercing member having a proximal end, a sharpened distal end, and an outer surface, said elongate piercing member being:
   (a) initially deployable in an "assembled" position within the lumen of the tubular sheath such that the sharpened distal end of the elongate member extends beyond the distal end of the catheter sheath; and
   (b) subsequently proximally withdrawable to a "retracted" position outside the lumen of said tubular sheath;
   a shielding means initially incorporated within said catheter assembly, said shielding means being operative to attach to and shield the sharpened distal end of said elongate piercing member as said elongate piercing member is moved from its "assembled" position to its "retracted" position;
   engagement means formed on the outer surface of said elongate piercing member; and
   a catch means comprising a spring ferrule incorporated in said shielding means and configured to engage said engagement means;
   said catch means being sized, configured, and positioned to interact with said engagement means as said elongate piercing member is moved from its "assembled" position to its "retracted" position; and
   said interaction between said catch means and said engagement means being operative to facilitate attachment of said shielding means to the distal end of said elongate piercing member.

2. The catheter assembly of claim 1 wherein said tubular sheath comprises a generally pliable, tubular catheter.

3. The catheter assembly of claim 1 wherein said elongate piercing member comprises a needle having an inner lumen extending axially therethrough.

4. The catheter assembly of claim 1 further comprising a hub formed on the proximal end of the tubular sheath, said hub having a hollow inner bore sized and configured such that at least a portion of said elongate member will pass therethrough when said elongate member is in its initial "assembled" position, and further such that said hollow inner bore will be fluidly communicative with the lumen of said catheter sheath when the elongate member is moved to its "retracted" position.

5. The catheter assembly of claim 1 wherein:
said shielding means further comprises at least one notch sized and configured to receive the sharpened distal tip of the elongate piercing member therein;
said at least one notch being positioned within said shielding means such that the sharpened distal tip of the elongate piercing member will become nested within said notch when the interaction between said catch means and said engagement means occurs.

6. The catheter assembly of claim 1 wherein said engagement means comprises an annular shoulder formed about the outer surface of said elongate piercing means.

7. The catheter assembly of claim 1 wherein the distal end of said catheter sheath is positioned distal to said annular shoulder when said elongate piercing member is deployed in its "assembled" position.

8. The catheter assembly of claim 1 wherein the distal end of said catheter sheath is positioned proximal to said annular shoulder when said elongate piercing member is deployed in its "assembled" position and wherein said catheter sheath is capable of dilating sufficiently to permit said annular shoulder to pass through the catheter lumen as the elongate piercing member is moved from its "assembled" position to its "retracted" position.

9. The catheter assembly of claim 8 wherein said catheter sheath is formed of material which, upon contact with body fluid, will expand sufficiently to permit the said passage of the annular shoulder through the cannula lumen.

10. A catheter assembly comprising:
a tubular sheath having a proximal end, a distal end, and an inner lumen extending axially therethrough;
an elongate piercing member having a proximal end, a sharpened distal end, and an outer surface, said elongate piercing member being:
  (a) initially deployable in an "assembled" position within the lumen of the tubular sheath such that the sharpened distal end of the elongate member extends beyond the distal end of the catheter sheath; and
  (b) subsequently proximally withdrawable to a "retracted" position outside the lumen of said tubular sheath;
a shielding means initially incorporated within said catheter assembly, said shielding means being operative to attach to and shield the sharpened distal end of said elongate piercing member as said elongate piercing member is moved from its "assembled" position to its "retracted" position;
said shielding means further comprising:
  a general frusto-conical body having a distal end, a proximal end, and an axial bore;
  upper and lower internally notched lobes formed on the distal end of said generally frusto-conical body;
  a spring ferrule positioned within the axial bore of said generally frusto-conical body; and
  engagement means formed on the outer surface of said elongate piercing member;
  said spring ferrule being sized, positioned, and configured to abut against said engagement means as said elongate piercing member is being proximally withdrawn from its "assembled" position to its "retracted" position;
  the distance between said spring ferrule and the internal notches of said lobes being such that the distal tip of the elongate piercing member is positionable in one of said notches while said spring ferrule is in direct abutment with said engagement means;
engagement means formed on the outer surface of said elongate piercing member; and
a catch means comprising a spring ferrule incorporated in said shielding means and configured to engage said engagement means;
said catch means being sized, configured, and positioned to interact with said engagement means as said elongate piercing member is moved from its "assembled" position to its "retracted" position;
said interaction between said catch means and said engagement means being operative to facilitate attachment of said shielding means to the distal end of said elongate piercing member.

* * * * *